United States Patent [19]
Rodgers et al.

[11] Patent Number: 6,039,091
[45] Date of Patent: Mar. 21, 2000

[54] FILLING DEVICE FOR USE IN MANUFACTURING OF GEL FILLED PROSTHESES

[75] Inventors: Kenneth W. Rodgers, Flower Mound; Gary D. Strong, Bedford; Michael C. Christy, Plano; Russell C. Mason, Fort Worth, all of Tex.

[73] Assignee: Mentor Corporation, Santa Barbara, Calif.

[21] Appl. No.: 09/128,090

[22] Filed: Aug. 3, 1998

[51] Int. Cl.⁷ .................................................. B65B 3/28
[52] U.S. Cl. .................................. 141/83; 141/59; 141/65; 623/7
[58] Field of Search ................................ 264/40.4; 623/7, 623/8, 901; 141/59, 61, 65, 83, 329, 7; 425/140

[56] References Cited

U.S. PATENT DOCUMENTS

| | | | |
|---|---|---|---|
| 4,726,404 | 2/1988 | Haber et al. | 141/59 |
| 5,258,026 | 11/1993 | Johnson et al. | 623/8 |
| 5,632,777 | 5/1997 | Petrick | 623/11 |
| 5,888,220 | 3/1999 | Felt et al. | 623/17 |
| 5,896,897 | 4/1999 | Lewis et al. | 141/39 |
| 5,941,909 | 8/1999 | Purkait | 623/11 |

*Primary Examiner*—Jan H. Silbaugh
*Assistant Examiner*—Dae Young Lee
*Attorney, Agent, or Firm*—Blakely, Sokoloff, Taylor & Zafman LLP

[57] ABSTRACT

Filling device and method for use in manufacturing of gel filled prostheses which provides fast and accurate filling of prosthesis shells without deterioration of the gel or induction of air into the prosthesis. The filling method utilizes a dual port cannula for penetrating a preslit fill port on a prosthesis shell, the cannula having one port coupled through a flexible tube to a peristaltic pump supplied with gel under pressure, and a second port coupled through a flexible tube to a vacuum system. The cannula and prosthesis shell being filled are supported on a scale, with the flexible tubes being disposed so that pressure variations in the tubes do not effect the scale readings.

20 Claims, 1 Drawing Sheet

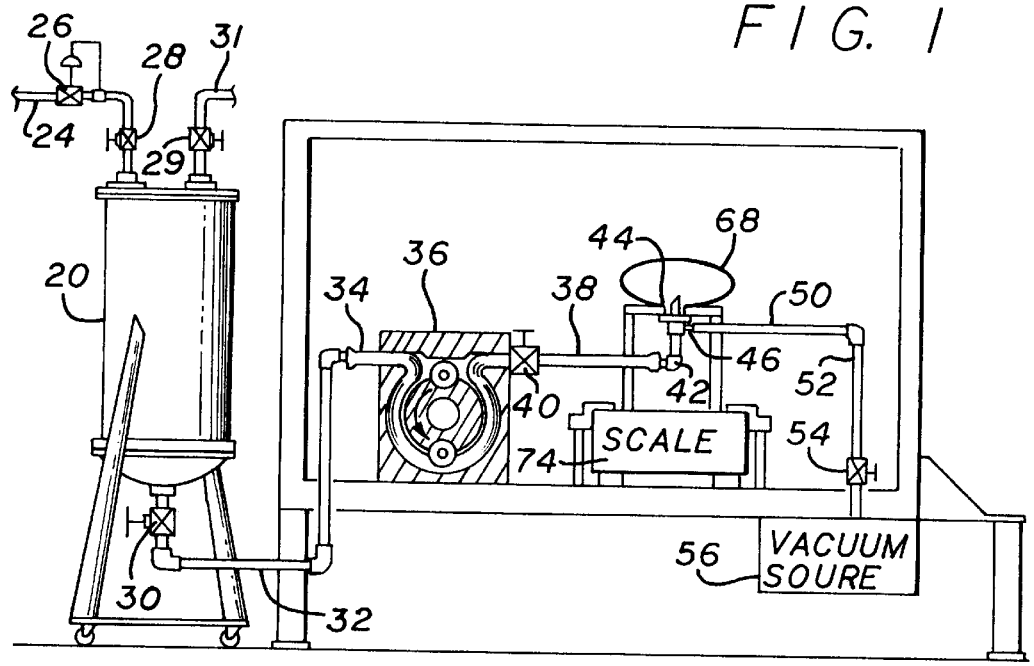
FIG. 1
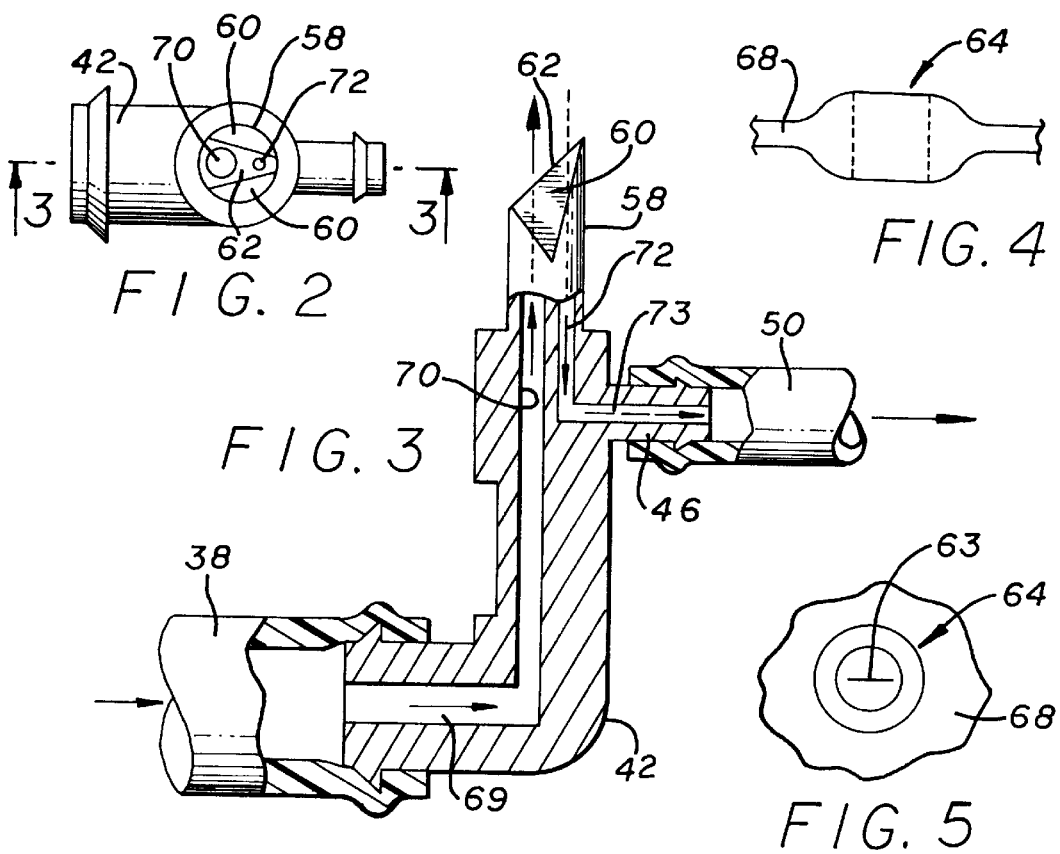
FIG. 2
FIG. 3
FIG. 4
FIG. 5

FILLING DEVICE FOR USE IN MANUFACTURING OF GEL FILLED PROSTHESES

BACKGROUND OF THE INVENTION

1. Field of the Invention

The present invention relates to filling devices and methods for the filling of shells of prosthetic devices, such as mammary and penile implants.

2. Background Information

The preferred embodiment of the present invention is intended for the filling of mammary prostheses with a new, alternate polymeric filling material. While other types of polymers have been successfully filled into an implantable device, this alternate gel, because of its own special characteristics, called for the reevaluation of conventional filling equipment and techniques, and the development of new and unique equipment and techniques to assure the desired end result. The polymer in the alternate filler is a cross linked (poly) acrylamide, highly viscous (~130–240K centipoise), cohesive (the ability to maintain structure within its domains upon placement of stress), and shear sensitive (non-Newtonian). The polymers physical characteristics related to viscosity, molecular weight distribution and number and flow characteristics are at their peak during fill operations.

In the design and implementation of a novel mammary prosthesis filling device/system, several critical attributes must be resolved. These attributes include: (1) the filling of implantable devices with the alternate gel in a "bubble free" physical state which allows optimum conditions for radiolucency analysis; (2) a process which provides consistently accurate weight or volume dispensing of a gelatinous material; (3) a device which simultaneously pulls a vacuum on an implant shell to evacuate all contained air therein; and (4) minimizing the shearing effect associated with kinetic pressure typical of current filling systems.

Expanding on these attributes, it is important to recognize that the ability to fill a device "bubble free" is critical, as it relates to the ability of a surgeon or appropriate hospital staff member to accurately interpret x-rays for symptoms associated with breast cancer, tumor growth, device wrinkles, capsular contraction(s) and the like. A bubble in the device will show as a spot on an x-ray, leading to potential misdiagnosis or unnecessary medical concern.

In filling of the device, a specification of ±2.0% (by weight or volume) is critical, as a mammary prosthesis filled with the alternate gel cannot be weight or volume adjusted once it has been implanted (unlike saline filled prostheses). The design and size of the pump is critical in meeting the requirements of the specific polymer being used. Any positive-displacement pump (piston, rotary lobe, rotary piston, progressive cavity, peristaltic, etc.) will function properly with low viscosity Newtonian fluids. With shear sensitive fluids, the pump design is restricted mostly to peristaltic, progressive cavity, rotary lobe or rotary piston pumps. The calibration of the pump flow rate (speed of cycles) piping or tubing (type, ID, OD), pressure (polymeric force) and filling speed are all critical in meeting the stringent specification, as practically and efficiently as possible.

Providing an "air-free" environment in the prosthetic device shells to be filled serves two purposes: the first being that the alternate filler will never contact outside air sources which are known to carry contaminants, and the second being that upon filling with the gel, pocketed void areas that could encapsulate air are not present, thus preventing areas in the device which would form air pockets and have to be evacuated by alternate methods.

The final area, and one of the most critical, is the shear thinning of the polymer as it is being injected into the mammary device (shell). The polymer of the alternate gel is non-Newtonian (viscosity breakdown with increased shear rates) and must be handled in a system that prevents excessive shearing and introduction of unnecessary heat. While the polymer will eventually be subjected to the forces associated with steam sterilization (heat and pressure), excessive physical deformation is not acceptable in maintaining a final polymeric viscosity to provide the desired "feel".

Filling of devices comparable to the mammary and/or penile devices currently manufactured by Mentor Inc., assignee of the present invention, range from syringe injection to filling ports. With polymers such as silicones, the viscosity of the polymer is 50–75% lower at the filling operation than the alternate filler considered herein.

SUMMARY OF THE INVENTION

Filling device and method for use in manufacturing of gel filled prostheses which provides fast and accurate filling of prosthesis shells without deterioration of the gel or induction of air into the prosthesis. The filling method utilizes a dual port cannula for penetrating a preslit fill port on a prosthesis shell, the cannula having one port coupled through a flexible tube to a low shear pump supplied with gel under pressure and not exposed to air, and a second port coupled through a flexible tube to a vacuum system. The cannula and prosthesis shell being filled are supported on a scale, with the flexible tubes being disposed so that pressure variations in the tubes do not effect the scale readings. Use of a vacuum port for the cannula of an appropriately small size will quickly and adequately initially evacuate a prosthesis shell, yet prevent significant ingestion of the gel into the vacuum system during filling because of the cohesiveness of the gel. Various other novel aspects of the method and apparatus are disclosed.

BRIEF DESCRIPTION OF THE DRAWINGS

The features and advantages of the present invention will become apparent from the following detailed description of the present invention in which:

FIG. 1 is a schematic diagram of a preferred embodiment of the present invention apparatus.

FIG. 2 is a top view of the cannula 44 of FIG. 1.

FIG. 3 is a partial cross-section of the cannula 44 taken on an expanded scale along line 3—3 of FIG. 2.

FIG. 4 is a side cross section illustrating the reinforced area or filling port of a prosthesis shell.

FIG. 5 is a face view of the filling port of FIG. 4.

DESCRIPTION OF THE PREFERRED EMBODIMENT

First referring to FIG. 1, a preferred embodiment of the present invention may be seen. The filling system of the preferred embodiment of the present invention utilizes a peristaltic pump to meter the selected gels (viscoelastic compositions) into shells or encapsulated units supported on a platform weighing table mounted on a calibrated digital scale. In particular, the weighing table is designed with legs that are mated with load bearing cells to the prescribed scale for obtaining accurate weight determination. The preferred embodiment is intended to be utilized with gels having an initial viscosity of 500–1000 cps at the time of mixing, which viscosity will gradually increase to a viscosity of 170,000±30,000 cps. The specific pump used has the ability to receive polymeric material under pressure and continually discharge the material at a constant flow rate, to a maximum of 250,000 cps.

The specific gel used with the preferred embodiment is a polyacrylamide hydrogel formed by approximately 3.0% to 5% by weight polyacrylamide polymer in a saline solution. The gel is formed by first stirring or agitating the saline solution in a vacuum to de-aerate the same, and then mixing the polyacrylamide polymer into the saline solution, again under a vacuum. Thereafter, while the gel is still in a very near liquid state (before it fully hydrates), the gel is transferred into a stainless steel pressure vessel 20 (FIG. 1) through a connection to valve 30 using a vacuum provided through valve 29 from a vacuum source connected to line 31, and then isolated with valve 30. The pressure vessel is then coupled through valve 30 and line 32 to the flexible hose 34 of the peristaltic pump 36. An autoclaveable bag used as a bladder is mounted to the inside top of the pressure vessel, to provide uncontaminated positive pressure to the gel. In the preferred embodiment, the bag is then inflated with nitrogen provided through line 24, regulator 26 and control valve 28 to a pressure of approximately 60 psig (approximately 4 atmospheres). Alternatives to the bag could be any device that provides positive pressure to the gel while separating the gel from any contaminate or gas that could permeate the surface of the gel and create gas pockets (i.e., a mechanically, hydraulically or pneumatically driven piston, septum or platen).

The discharge of the peristaltic pump's 36 flexible hose 32, having valve 40 therein, being coupled to the first inlet 42 of cannula 44. The second inlet 46 of cannula 44 is coupled through a flexible line 50 and through valve 54 to a vacuum source 56 powered by a conventional vacuum pump, preferably creating a vacuum of approximately 26 to 28 inches of mercury.

The pressure vessel 20 is coupled through a valve 30 and line 32 to the flexible hose 34 of the peristaltic pump 36, with the flexible hose 34 or an extension thereof 38, having a valve 40 therein, being coupled to a first inlet 42 of cannula 44. The second inlet 46 of cannula 44 is coupled through flexible line 50 to a rigid line 52, and through a valve 54 to a vacuum source 56 powered by a conventional vacuum pump, preferably creating a vacuum of approximately 26 to 28 inches of mercury.

The cannula itself may be seen in FIG. 2, and in FIG. 3 which is a partial cross-section taken on an expanded scale along line 3—3 of FIG. 2. The cannula itself has a circular section 58, in the preferred embodiment approximately ⅜ inch in diameter, with flat regions 60 tapering the cross-section 58 to an inclined, flat wedge-shaped region 62 forming the end of the cannula. In that regard, the mammary prostheses shells to be filled with the preferred method and apparatus of the present invention have a reinforced area or filling port, generally indicated by the numeral 64 of FIG. 4, which is pre-slit with a surgical knife to form slit 63 shown in the face view of the filling port 64 of FIG. 5. The end 62 of the cannula 44 may be readily forced through the pre-slit filling port of the prosthesis shell 68 so as to form an airtight seal with respect thereto without damage to the filling port, yet with end 62 and the edges associated therewith being sufficiently blunt so as to generally not be capable of damaging the opposite wall of the prosthesis shell, either when penetrating the filling port with the cannula or, as shall subsequently be described, when evacuating all the air from the prosthesis shell prior to the filling thereof.

Referring again to FIG. 3, the first inlet 42 for the cannula has a horizontal cylindrical passage 69 in communication with a vertical cylindrical passage 70 extending through the face 62 of the cannula (see also FIG. 2). In the preferred embodiment, the vertical passage 70 (as well as the corresponding opening in the top surface 62 of the cannula) is approximately 3/16 inch in diameter. This diameter preferably will be as small as reasonably possible to reduce the size of the cannula, though for the specific gels with which the preferred embodiment of the present invention is intended to be used, 3/16 inch in diameter was found to be about the minimum diameter through which adequate flow rates could be obtained using reasonable pressures encouraging movement of the gel. The opening 69, on the other hand, preferably is larger than opening 70, with the flexible tubing 38 normally being the same size or larger in inner diameter than the opening 69 so as not significantly increase the overall restriction to gel flow. Further reduction in the restriction of flow may be achieved by using a gradual 90° curve in the junction of passageways 69 and 70 rather than the sharp 90° transition schematically shown.

The second inlet 46 has a cylindrical passageway 72 which is considerably smaller than the passageway 70 in the cannula, as this opening is for evacuating the prosthesis shell. In the preferred embodiment, passageway 72 is 1/16 inch in diameter, being coupled through passageway 73 of ⅛ inch in diameter to flexible hose 50 of a still larger inner diameter, such as ¼ inch diameter. The flexible hose 50 is sufficiently thick so as to be self-supporting to avoid collapsing when used as a vacuum line. The diameter of the passageway 72 is sufficiently small so that even when the prosthesis shell is highly evacuated, the resulting approximately one atmosphere differential pressure tending to force the gel into passageway 72 is inadequate to do so because of the cohesiveness of the gel. This is an important aspect of the invention, as it allows maintenance of the vacuum during filling without filling at least part of the vacuum system, requiring extensive cleaning or purging before filling the next prosthesis shell. It also avoids weight errors that could otherwise arise because of variations in the amount of gel in the vacuum side of the cannula and the part of the flexible hose contributing to the weight reading of the scale. Finally of course, it avoids loss of gel, making the filling operation both expedient and efficient.

Referring again to FIG. 1, a mammary prosthesis shell 68 having its fill port penetrated by the cannula 44 for communication through openings 70 and 72 in the cannula with the interior of the shell may be seen. As shown therein, the cannula 44 and prosthesis shell 68, as well as some portion of the flexible tubes 38 and 50, are supported by scale 74 so that the scale will respond not only to the weight of the filling material added to the prosthesis shell 68, but to the weight of the various other components of the system supported thereon. In that regard, the scale should be an electronic scale having its tare set to take into account the weight of the various components including an unfilled prosthesis shell thereon, so that the weight of the gel added during the shell filling operation will be directly determined, or alternatively the beginning and final weights may be determined through use of the scale, with the weight of the gel equaling the difference between the starting and final weights.

In any event, once the de-aerated gel has been properly mixed and hydrated in the pressure vessel 20, and pressurized as previously described, the valves 38 and 30 will be opened and the peristaltic pump 36 will be turned on. This will have the effect of priming the system, filling the line from the pressure vessel 20 to the peristaltic pump 36, the pump itself and the line to the cannula 44, as well as the cannula itself with gel. Once the system is primed as described and any excess gel which came out of the cannula during the priming is removed, a prosthesis shell 68 (FIG. 1) to be filled is placed on the scale 74 and the fill port forced downward over cannula 44 against the controlling base, at which point the cannula will project inward through the pre-slitted fill port on the shell into the interior of the shell. Then valve 54 in the vacuum system is opened so that the cannula will evacuate the prosthesis shell. Then the peristaltic pump 36 is turned on to fill the shell, the filling being complete when the change in the scale reading is a predetermined value indicating that the prosthesis shell 68 has been filled with a predetermined amount, by weight, of the gel during the filling. The gel is fed into the shell through the filling cannula at a rate of 20 to 400 ml(cc) per minute. As the filling is proceeding, the vacuum may be left on or turned off as desired, as even if turned off, vacuum will remain in lines 50 and 52 to keep air expelled from the prosthesis shell. During filling, the pump valve is opened fully, and upon meeting the specifications for the fill weight, the valve is closed and the pump 36 is stopped, preventing over fill or residuals. Even after filling, the vacuum port 62 on the cannula, being the last portion of the cannula to be removed from the fill port, has been found to have the further advantageous effect of cleaning any very small amount of gel which might otherwise be trapped in the fill port. Finally, after removal of the filled prosthesis shell from the cannula and scale on which the cannula is supported, the vacuum may be turned off, if not already off, and the fill port may be permanently sealed with an appropriate silicon rubber adhesive.

After removal of a filled prosthesis from the filling system shown in FIG. 1, the vacuum side of the filling station should be examined and cleaned as necessary to remove any gel debris which possibly could have been ingested into the vacuum side of the cannula. For this purpose, it is convenient to use clear plastic flexible hose, both on the filling side and on the vacuum side of the cannula, so that on the filling side any air bubbles in the hose may be observed, and in the vacuum side any presence of gel may be observed. Once the vacuum system has been checked, and cleaned if necessary, the next prosthesis shell may be mounted on the cannula and filled as herein before described. Since the filling lines and filling port of the cannula are filled with gel to the same extent both before and after filling a prosthesis, there is no net change in the weight sensed by the scale from the filling system itself. Accordingly, the weight measured after filling minus the weight measured before filling of each prosthesis is a very accurate measure of the weight of gel added to the prosthesis during the filling operation.

In the prior description, it was noted that in the preferred embodiment, the pressure vessel 20 is pressurized to approximately 60 Psig. The reason for this is that a peristaltic pump, while normally being self priming, may only reduce the pressure at the inlet thereof so as to create a differential pressure encouraging flow to the pump inlet of something less than one atmosphere. In general, however, the gels for which the present invention is intended to be used, for the tubing size appropriate for the application, will not generally flow without a higher differential pressure encouraging the flow. Accordingly, even if once primed, the peristaltic pump will still generally not continuously draw gel into the pump unless the gel itself is pre-pressurized to force the same to the pump, or at least to grossly reduce the suction required at the pump input to draw gel from the pressure vessel thereto. Alternatively, the pressure in pressure vessel 20 may exceed that required to cause flow of the gel through the filling system, in which case the peristaltic pump, being a form of substantially positive displacement pump, functions more as an on-off control and metering device as opposed to a pump in the strict sense. Thus, as used herein and in the claims, it is to be understood that "pump" and "peristaltic pump" are used in a general sense to designate a pump and a peristaltic pump type device, respectively, whether truly pumping (causing the flow of) the gel or serving as an on-off and a flow metering device.

The prosthesis shell filling method and apparatus of the present invention for filling a prosthesis shell with a gel, particularly of the characteristics described, overcomes a number of problems which the inventors encountered with other methods and apparatus, to provide a fast, accurate, repeatable and efficient prosthesis filling operation. By way of example, in the present invention method and apparatus, the cannula and a portion of the flexible lines coupled thereto, and the portion of the gel within the corresponding portion of the gel supply line to the cannula, are supported by the scale and accordingly provide a weight offset to the scale for the weight readings that are actually taken. Ideally, the scale should not be subject to such offset, as at least in theory, more sensitive readings may be made if the range of the scale could be less. In practice, however, if the cannula 44 is not supported by the scale and connected to the filling and vacuum system through flexible hoses, but instead is supported independent of the scale by rigid tubing for the fill and evacuation lines, or by some other means, it has been found that while the soft shell of the prosthesis is still supported by the scale, on initial filling of the prosthesis shell, the cohesiveness of the gel will cause the gel to push upward against the shell from the cannula. This will result in readings during filling and immediately after shutting off the peristaltic pump which are lower than they should be. Over a period of time, however, the gel will tend to slump or relieve itself, resulting in the scale providing a higher reading than upon immediately stopping the filling process.

Similarly, if the cannula of FIG. 1 is supported above the scale table and pointing down so that the soft shell of the prosthesis is supported by the table, it has been found that the reverse occurs. The initial scale reading immediately after stopping filling is higher than after a period of time, the cohesiveness of the gel initially pushing downward on the scale from the cannula before relieving itself with time. In either case, the repeatability of results was poor, and therefore the effect encountered could not be accurately accounted for.

Similarly, if the fill and vacuum connections to the cannula are not orthogonal to the cannula itself (horizontal), such as by way of example, using flexible tubes 38 and 50 (FIG. 1) which curve upward to connect to a cannula, it was found that changes in pressure in the flexible tubes, particularly the fill tube, caused by resistance to flow of the gel, created a variable vertical force on the scale table, giving variable and erratic readings not truly indicative of the weight of gel currently being added or previously added to the prosthesis.

Other possibilities tested include a side discharge cannula (a basketball inflater type cannula) and the use of a cannula having a single port and two-way valve to controllably couple that single port to a vacuum system or a supply of gel. The side discharge cannula worked well in preventing the prosthesis shell from collapsing and damaging itself when the vacuum was drawn, though the attainable flow rate of gel there through during filling was too low to be considered a most viable option. The single port cannula, on the other hand, while maximizing the size of the fill port (which is also the vacuum port) for the cannula, has other disadvantages in comparison to the present invention. In particular, when a prosthesis shell is evacuated, the same collapses to substantially zero volume, or at least a very, very small volume, so that the prosthesis is substantially fully evacuated, even if the vacuum is substantially less than perfect. In the case of the single port cannula, however, the cannula itself does not collapse in the presence of a vacuum, with the air remaining in the cannula because of the imperfect vacuum then being swept into the prosthesis when the filling begins. While the use of de-aerated gel as herein before described might provide adequate solubility for the air to absorb the same to eliminate small air bubbles, such a configuration still has a much higher vacuum capability requirement than in the preferred embodiment of the invention described herein. Also, since the cannula becomes filled with gel during the filling operation, if that gel is not removed from the cannula before the next filling operation, the same will be ingested into the vacuum system, requiring some form of recovery if the same is not wasted, and potentially interfering with the accurate weighing of the filled prosthesis because of variable amounts of the gel which might cling to the walls of the flexible tubes in the vacuum system. Also, since the gel is formed from an aqueous solution, the extent of the vacuum and the duration the gel may be subjected thereto may be limited if alteration of the gel surface exposed to the vacuum is to be prevented.

The advantages the present invention method and apparatus offers over current filling systems are numerous, unique and novel. This design allows implantable devices or void-volume devices to be filled and monitored for weight simultaneously, which provides for better control and operator accuracy. Secondly, a cohesive polymer can be filled at a rate which allows optimum flow rates without the shearing which is prevalent with a cannula of other designs. This process allows for evacuation of air initially entrapped in the shell (final device) and provides an environment which prevents the introduction of foreign particles. Simultaneous filling and weighing of a unit can be achieved to provide the user a device filled within a ratio of ±2.0% based on weight or volume in a mammary prosthesis. This process does not degrade polymers that are sensitive to high shear or to heat.

The ability to maintain a constant flow rate is critical so as to maintain a fill volume/weight that can be statistically controlled within a 1.33 CpK. The design of the filling cannula prevents damage to or punctures in the shell which could be catastrophic if not found. This design can be used to fill viscous materials into an open or closed container, a two-step, one puncture process for filling in-vitro vials with an anti-coagulant under vacuum, or utilization of both fill bores (vacuum and fill) to fill epoxy type resins/polymers using the port size of the bores to meter the liquids. Practically any polymeric material (epoxy, organics, urethanes, foam base, solvent(s), etc.) which requires the need to be filled or injected into a pressure or vacuum controlled environment would benefit from use of embodiments of the present invention.

The filling cannula's design comprises a device which is constructed of two ports, each supplying specific operations to the final filling attribute. The first, the side port, is used to pull a vacuum for full exhaustion of air. The second port, a larger continual port is used for filling of the selected gels. This port allows the gel to flow at a controlled rate for optimizing the low-viscosity characteristic of the selected polymer, which aides in the prevention of shear thinning of non-Newtonian polymers.

The pump, and vacuum lines of flexible silicone tubing, prevent shear induction into the polymer as it moves along the tubular walls. The tubing selected prevents cross contamination with the silicone (i.e., leechables), along with preventing air induction into the flowing gel prior to shell injection.

Both (gel) pump and vacuum lines have rate controlling valves which regulate the removal of air and the introduction of filler material. The vacuum valve is opened during the shell evacuation and preferably closed mechanically upon introduction of the filler into the cannula tip. This allows for a shell (device) which can be filled to a designated volume without the residence of air. Since the system provides a filled device air-free, the potential for growth of microbials (i.e., endotoxins, bioburdens, etc.) is eliminated due to the fact that airborne particles will not be introduced into the device because of the enclosed filling system.

The preferred embodiment disclosed herein utilizes a peristaltic pump, which has the advantage of the pumping element not coming into contact with material being pumped. Other pumps that could be considered for use in the filling process include diaphragm/dual diaphragm pumps (having limited contact with the pumped material), eccentric-cam pumps (including flexible-liner pumps—a non-lined pump exposes the pumping material to all of the moving and static surfaces of the pump, while the lined pump only exposes the liner to the pumped material), lobe pumps (single and multi-lobe), progressing cavity pumps (screw pumps), and flexible impeller pumps. Not all of these pumps have the same advantage (that is, no pumping element in contact with the pumped material) that peristaltic pumps (flexible tubing pump) have, though all of them are, however, low shear pumps. In that regard, a low sheer pump as used herein is used to denote a pump which will pump or meter a sheer sensitive material without substantial change in the physical properties of the shear sensitive material, such as viscoelastic compositions.

While a certain exemplary embodiment of the present invention has been described and shown in the accompanying drawings, it is to be understood that such embodiment is merely illustrative of and not restrictive on the broad invention, and that this invention is not limited to the specific constructions and arrangements shown and described, since various other modifications may occur to those ordinarily skilled in the art.

What is claimed is:

1. Prosthesis filling apparatus comprising:
   a cannula having first and second ports for insertion through a fill port on a prosthesis shell to provide communication with an interior of the prosthesis shell through the first and second ports;
   a source of filling material;
   a low shear pump coupled to the source of filling material;
   a first flexible hose coupled between the low shear pump and the first port on the cannula;
   a vacuum source;
   a second flexible hose coupled between the vacuum pump and the second port on the cannula;
   a weight measuring scale;
   the cannula being positioned on the scale so that the scale will respond to the change in weight of a prosthesis, the fill port of which is penetrated by the cannula, the first and second flexible hoses being configured to not interfere with the free operation of the scale.

2. The filling apparatus of claim 1 wherein portions of the first and second hoses are adjacent the scale, said portions being substantially horizontal.

3. The filling apparatus of claim 1 wherein the source of filling material is a source of filling material under pressure.

4. The filling apparatus of claim 3 wherein the filling material is under pressure exerted in a manner to isolate the filling material from contact with a gas.

5. The filling apparatus of claim 1 wherein the source of filling material is a source of filling material under a pressure adequate to cause flow of the filling material through the cannula.

6. The filling apparatus of claim 1 wherein the source of filling material is a source of filling material under a pressure less than required to cause flow of the filling material through the cannula.

7. The filling apparatus of claim 1 wherein the tare of the weight measuring scale is set to include the weight of the cannula, the prosthesis shell to be filled, portions of the first and second flexible hoses supported by the scale, and that portion of the filling material within the first flexible hose which is supported by the scale.

8. The filling apparatus of claim 1 wherein the weight measuring scale is an electronic scale.

9. The filling apparatus of claim 1 wherein the low shear pump is a peristaltic pump.

10. The filling apparatus of claim 1 for use with a filling material comprising a viscoelastic material.

11. The filling apparatus of claim 10 wherein the size of the second port on the cannula is less than a size through which the vacuum will cause flow of the filling material through the second port.

12. The filling apparatus of claim 10 wherein the filling material comprises a polyacrylamide gel.

13. The filling apparatus of claim 12 wherein the polyacrylamide gel comprises a polyacrylamide hydrogel formed by approximately 3.0% to 5% by weight polyacrylamide polymer in a saline solution.

14. Prosthesis filling apparatus for filling a prosthesis shell with a viscoelastic material comprising:
   a cannula having first and second ports for insertion through a fill port on a prosthesis shell to provide communication with an interior of the prosthesis shell through the first and second ports;
   a source of filling material under pressure, the filling material being isolated from air;
   a low shear pump coupled to the source of filling material;
   a first flexible hose coupled between the low shear pump and the first port on the cannula;
   a vacuum source;
   a second flexible hose coupled between the vacuum pump and the second port on the cannula, portions of the first and second hoses being adjacent the scale, said portions being substantially horizontal;
   a weight measuring scale;
   the cannula being positioned on the scale so that the scale will respond to the change in weight of a prosthesis, the fill port of which is penetrated by the cannula, the first and second flexible hoses being configured to not interfere with the free operation of the scale.

15. The filling apparatus of claim 14 wherein the source of filling material is a source of filling material under a pressure adequate to cause flow of the filling material through the cannula.

16. The filling apparatus of claim 14 wherein the source of filling material is a source of filling material under a pressure less than required to cause flow of the filling material through the cannula.

17. The filling apparatus of claim 14 wherein the tare of the weight measuring scale is set to include the weight of the cannula, the prosthesis shell to be filled, portions of the first and second flexible hoses supported by the scale, and that portion of the filling material within the first flexible hose which is supported by the scale.

18. The filling apparatus of claim 14 wherein the low shear pump is a peristaltic pump.

19. The filling apparatus of claim 14 wherein the viscoelastic material comprises a polyacrylamide gel.

20. The filling apparatus of claim 19 wherein the polyacrylamide gel comprises a polyacrylamide hydrogel formed by approximately 3.0% to 5% by weight polyacrylamide polymer in a saline solution.

* * * * *